United States Patent [19]

Beaulieu et al.

[11] Patent Number: 5,700,780
[45] Date of Patent: Dec. 23, 1997

[54] ANTIVIRAL PEPTIDE DERIVATIVES HAVING A 2-OXOALKYL AMINO ACID SIDE CHAIN

[75] Inventors: Pierre Louis Beaulieu, Montreal; Robert Déziel, Mont-Royal; Pierre Lavallée, Rosemere, all of Canada

[73] Assignee: Boehringer Ingelheim (Canada), Ltd., Laval, Canada

[21] Appl. No.: 540,862

[22] Filed: Oct. 11, 1995

Related U.S. Application Data

[63] Continuation of Ser. No. 90,682, Jul. 13, 1993, abandoned, which is a continuation of Ser. No. 926,605, Aug. 7, 1992, abandoned, which is a continuation of Ser. No. 547,712, Jul. 3, 1990, abandoned.

[30] Foreign Application Priority Data

Jul. 7, 1989 [CA] Canada ........................ 605062

[51] Int. Cl.$^6$ ........................ A61K 38/00; C07K 5/00
[52] U.S. Cl. ........................ 514/17; 514/18; 530/329; 530/330; 530/331
[58] Field of Search ........................ 514/17, 18; 530/329, 530/330, 331

[56] References Cited

U.S. PATENT DOCUMENTS

| 4,795,740 | 1/1989 | Cohen et al. | 514/14 |
| 4,814,432 | 3/1989 | Freidinger et al. | 530/329 |
| 4,837,304 | 6/1989 | Garsky et al. | 530/328 |
| 4,845,195 | 7/1989 | Colonno et al. | 530/330 |
| 5,502,036 | 3/1996 | Adams et al. | 514/17 |

FOREIGN PATENT DOCUMENTS

| 0352000 | 1/1990 | European Pat. Off. |
| 0357332 | 3/1990 | European Pat. Off. |
| 0374097 | 6/1990 | European Pat. Off. |

OTHER PUBLICATIONS

Gaudreau et al., J. Biol. Chem. vol. 262, No. 26, pp. 12413–12416, Sep. 1987.

*Primary Examiner*—Cecilia J. Tsang
*Assistant Examiner*—Bennett Celsa
*Attorney, Agent, or Firm*—R. P. Raymond; M-E. M. Devlin; A. R. Stempel

[57] ABSTRACT

Disclosed herein are peptide derivatives of the formula $X[-NR^1-CH(R^2)-C(W^1)]_n-NH-CR^3(R^4)-C(W^2)-NR^5-CH[CH_2C(O)-Y]-C(W^3)-NH-CR^6-[CR^7-(R^8)-COOH]-C(W^4)-NH-CR^9(R^{10})-Z$ wherein X is a terminal group, for example, alkanoyl or phenylalkanoyl radicals, $R^1$ is hydrogen, alkyl or phenylalkyl, $R^2$, $R^4$ and $R^{10}$ am selected from amino acid or derived amino acid residues, $R^3$, $R^5$, $R^6$, $R^7$, $R^8$ and $R^9$ are hydrogen or alkyl, or $R^7$ and $R^8$ are joined to form a cycloalkyl, $W^1$, $W^2$, $W^3$ and $W^4$ are oxo or thioxo, Y is, for example, an alkyl or a cycloalkyl, Z is a terminal group, for example, COOH or $CH_2OH$, and n is 0 or 1. The derivatives are useful for treating herpes infections.

6 Claims, No Drawings

ANTIVIRAL PEPTIDE DERIVATIVES HAVING A 2-OXOALKYL AMINO ACID SIDE CHAIN

This is a continuation of application Ser. No. 08/090,682, filed Jul. 13, 1993 (abandoned), which is a continuation of application Ser. No. 07/926,605, filed Aug. 7, 1992 (abandoned), which is a continuation of application Ser. No. 07/547,712, filed Jul. 3, 1990 (abandoned).

FIELD OF THE INVENTION

This invention relates to peptide derivatives having antiviral properties and to means for using the derivatives to treat viral infections. More specifically, the invention relates to peptide derivatives (hereinafter called "peptides") exhibiting activity against herpes viruses, to pharmaceutical compositions comprising the peptides, and to a method of using the peptides to treat herpes infections.

BACKGROUND OF THE INVENTION

The family of herpes viruses is responsible for a wide range of infections that afflict humans and many important domestic animals. The diseases caused by these viruses range from bothersome cold sores to highly destructive infections of the central nervous system (encephalitis). The more common members of this family include herpes simplex virus (types 1 and 2) responsible for cold sores and genital lesions; varicella zoster virus which causes chicken pox and shingles; and Epstein-Barr virus which causes infectious mononucleosis. Although some significant advances have been made in the last decade in antiviral therapy, the need for effective, safe therapeutic agents for treating herpes viral infections continues to exist. For a recent review of current therapeutic agents in this area, see M. C. Nahata, "Antiviral Drugs: Pharmacokinetics, Adverse Effects and Therapeutic Use", J. Pharm. Technol., 3, 100 (1987).

The present application discloses a group of peptide derivatives having activity against herpes viruses. The relatively selective action of these peptides against herpes viruses, combined with a wide margin of safety, renders the peptides as desirable agents for combating herpes infections.

The association of peptides with anti-herpes activity is uncommon. Instances of reports of such an association include B. M. Dutia et al., Nature, 321, 439 (1986), E. A. Cohen et al., Nature, 321, 441 (1986), J. H. Subak-Sharpe et al., UK patent application 2185024, published Jul. 8, 1987, E. A. Cohen et al., European patent application 246630, published Nov. 25, 1987, R. Freidinger et al., European patent application 292255, published Nov. 23, 1988, and R. Freidinger et al., U.S. Pat. No. 4,814,432, issued Mar. 21, 1989. The subject peptides of the previous reports can be distinguished from the peptides of the present application by characteristic structural and biological differences.

SUMMARY OF THE INVENTION

The peptides of this invention are represented by formula 1

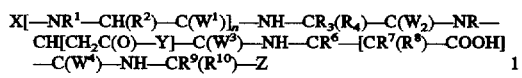

wherein X is (1–10C)alkanoyl, (1–10C)alkoxycarbonyl, benzoyl, benzoyl monosubstituted or disubstituted with a substituent selected from halo, hydroxy, lower alkyl, lower alkoxy, phenyl, 2-carboxyphenyl or benzyl, 2,2-diphenylacetyl, phenyl(1–10C)alkanoyl or phenyl(1–10C)alkanoyl monosubstituted or disubstituted on the aromatic portion thereof with a substituent selected from halo, hydroxy, lower alkyl, lower alkoxy or phenyl;

$R^1$ is hydrogen, lower alkyl or phenyl(lower)alkyl;

$R^2$ is lower alkyl, hydroxy(lower)alkyl or mercapto(lower)alkyl);

$R^3$, $R^5$, $R^6$ and $R^9$ each independently is hydrogen or lower alkyl;

$R^4$ is hydrogen, lower alkyl, hydroxy(lower)alkyl, mercapto(lower)alkyl, methoxy(lower)alkyl, methylthio(lower)alkyl lower cycloalkyl or (lower cycloalky)methyl;

$R^7$ and $R^8$ each independently is hydrogen or lower alkyl, or $R^7$ and $R^8$ together with the carbon atom to which they are attached form a lower cycloalkyl;

$R^{10}$ is lower alkyl, lower alkenyl or (lower cycloalkyl)methyl;

$W^1$, $W^2$, $W^3$ and $W^4$ each independently is oxo or thioxo;

Y is (1–14C)alkyl, lower cycloalkyl, lower alkyl monosubstituted with a lower cycloalkyl, phenyl(lower)alkyl, phenyl(lower)alkyl wherein the aromatic portion thereof is substituted with halo, lower alkyl or lower alkoxy, or (Het)-lower alkyl wherein Het represents a five or six membered heterocyclic radical containing one or two heteroatoms selected from nitrogen, oxygen or sulfur, Z is hydrogen, COOH, $CH_2COOH$, 5-1H-tetrazolyl, $COOR^{11}$ wherein $R^{11}$ is lower alkyl, $CH_2OH$, $CONR^{12}R^{13}$ wherein $R^{12}$ and $R^{13}$ each independently is hydrogen or lower alkyl, or $CON(R^{14})OH$ wherein $R^{14}$ is hydrogen or lower alkyl; and n is the integer zero or one;

or a therapeutically acceptable salt thereof.

A preferred group of the peptides of this invention is represented by formula 1 wherein X is (1–10C)alkanoyl, (1–10C)alkoxycarbonyl, benzoyl, benzoyl monosubstituted with halo, hydroxy, lower alkyl, lower alkoxy, phenyl, 2-carboxyphenyl or benzyl, 2,2-diphenylacetyl, phenyl (1–10C)alkanoyl or phenyl(1–10C)alkanoyl monosubstituted or disubstituted on the aromatic portion thereof with a substituent selected from halo, hydroxy, lower alkyl, lower alkoxy or phenyl; $R^1$ to $R^{10}$, inclusive, and $W^1$ to $W^4$, inclusive, are as defined hereinabove; Y is (1–14C)alkyl, lower cycloalkyl, lower cycloalkylmethyl, phenyl(lower) alkyl or (Het)-lower alkyl wherein Het is a heterocyclic radical selected from 2-pyrrolyl, 2-pyridinyl, 4-pyridinyl, 2-furyl, 2-isoxazolyl and 2-thiazolyl; Z is as defined hereinabove; and n is the interger zero or one; or a therapeutically acceptable salt thereof.

A more preferred group of the peptides is represented by formula 1 wherein X, $R^7$, $R^8$ and $R^{10}$ are as defined hereinabove; $R^1$ is lower alkyl; $R^2$ is lower alkyl or hydroxy (lower)alkyl; $R^3$, $R^5$, $R^6$ and $R^9$ each independently is hydrogen or methyl; $R^4$ is hydrogen, lower alkyl, hydroxy (lower)alkyl, methoxy(lower)alkyl, lower cycloalkyl or (lower cycloalkyl)methyl; $W^1$, $W^2$, $W^3$ and $W^4$ are oxo; Y is (1–14C)alkyl, lower cycloalkyl, lower cycloalkylmethyl, phenyl(lower)alkyl or pyridinyl(lower alkyl); Z is hydrogen, COOH, $CH_2COOH$, 5-1H-tetrazolyl, $CH_2OH$, $CONR^{12}R^{13}$ wherein $R^{12}$ and $R^{13}$ each independently is hydrogen or lower alkyl, or $CON(R^{14})OH$ wherein $R^{14}$ is hydrogen or lower alkyl; and n is the integer zero or one; or a therapeutically acceptable salt thereof.

A most preferred group of the peptides is represented by formula 1 wherein X is acetyl, 2-ethylbutanoyl, 4-methylpentanoyl, octanoyl, Boc, benzoyl, 2-biphenylylcarbonyl, 2-(2'-carboxy)biphenylylcarbonyl, phenylacetyl, phenylpropionyl, (4-hydroxyphenyl) propionyl or (3,4-dihydroxyphenyl)propionyl; $R^1$ is methyl; $R^2$ is 1-methylethyl, 1,1-dimethylethyl, 1-methylpropyl or 1-hydroxyethyl; $R^3$ is hydrogen or methyl; $R^4$ is hydrogen, lower alkyl, hydroxymethyl, 1-hydroxyethyl, 1-methoxyethyl, cyclopentyl or cyclohexylmethyl; $R^5$ is hydrogen or methyl; $R^6$ is hydrogen; $R^7$ and $R^8$ each independently is hydrogen, methyl, ethyl or propyl, or $R^7$ and $R^8$ together with the carbon atom to which they are joined form a lower cycloalkyl; $R^9$ is hydrogen or methyl; $R^{10}$ is 2-methylpropyl, 3-methylbutyl or 2,2-dimethylpropyl; $W^1$, $W^2$, $W^3$ and $W^4$ are oxo; Y is methyl, hexyl, heptyl, 1-methylheptyl, decyl, undecyl, cyclopentyl, cyclohexyl, cyclohexylmethyl or phenylpropylethyl; Z is hydrogen, COOH, $CH_2COOH$, 5-1H-tetrazolyl, $CH_2OH$, $CONR^{12}R^{13}$ wherein $R^{12}$ and $R^{13}$ each independently is hydrogen, methyl, ethyl or propyl, or $CON(R^{14})OH$ wherein $R^{14}$ is hydrogen or methyl; and n is the integer one; or a therapeutically acceptable salt thereof.

Included within the scope of this invention is a pharmaceutical composition comprising an anti-herpes virally effective amount of a peptide of formula 1, or a therapeutically acceptable salt thereof, and a pharmaceutically or veterinarily acceptable carrier.

Also included within the scope of this invention is a cosmetic composition comprising a peptide of formula 1, or a therapeutically acceptable salt thereof, and a physiologically acceptable carrier suitable for topical application.

An important aspect of the invention involves a method of treating a herpes viral infection in a mammal by administering to the mammal an anti-herpes virally effective amount of the peptide of formula 1, of a therapeutically acceptable salt thereof.

Another important aspect involves a method of inhibiting the replication of herpes virus by contacting the virus with a herpes viral ribonucleotide reductase inhibiting amount of the peptide of formula 1, or a therapeutically acceptable salt thereof.

Processes for preparing the peptides of formula 1 are described hereinafter.

DETAILS OF THE INVENTION

General

Alternatively, formula 1 can be illustrated as follows:

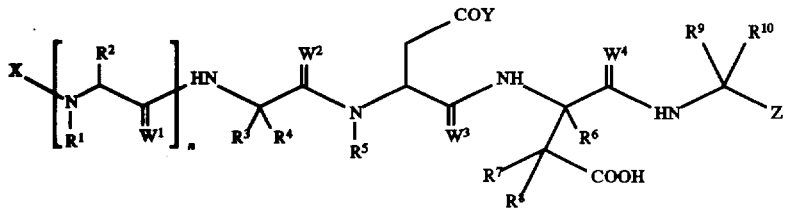

The term 'residue' with reference to an amino acid or amino acid derivative means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commision of Biochemical Nomenclature, see European Journal of Biochemistry 138, 9 (1984). For instance, Gly, Val, Thr, Ala, Ile, Asp, Ser and Leu represent the residues of glycine, L-valine, L-threonine, L-alanine, L-isoleucine, L-aspartic acid L-serine and L-leucine, respectively.

The asymmetric carbon atoms residing in the principal linear axis (i.e. the backbone) of the peptides of formula 1, exclusive of the terminal groups, have an S configuration. Asymmetric carbon atoms residing in the side chain of an amino acid or derived amino acid residue, including those in terminal groups, may also have the R configuration. Furthermore, with respect to disubstituted benzoyl and disubstituted phenyl(1–10C)alkanoyl as defined for X of peptides of formula 1, the substituents are selected on, the basis that they do not interfere with each others presence.

The term 'halo' as used herein means a halo radical selected from bromo, chloro, fluoro or iodo.

The term "lower alkyl" as used herein, either alone or in combination with a radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1,1-dimethylethyl.

The term "lower alkenyl" as used herein means straight chain alkenyl radicals containing two to six carbon atoms and branched chain alkenyl radicals containing three to six carbon atoms and includes vinyl, 1-propenyl, 1-methylethenyl, 2-methyl-1-propenyl, 2-methyl-2-propenyl and 2-butenyl.

The term "lower cycloalkyl" as used herein, either alone or in combination with a radical, means saturated cyclic hydrocarbon radicals containing from three to six carbon atoms and includes cyclopropyl, cyclobutyl, cyclopentyl and cyclohexyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tertiary-butyloxy.

The term "(1–14C)alkyl" as used herein means straight and branched chain alkyl radicals containing from one to fourteen carbon atoms. The term "(1–10C)alkoxycarbonyl" as used herein, means straight and branched chain alkoxycarbonyl radicals containing from one to ten carbon atoms in their alkoxy portion and includes, for example, ethoxycarbonyl, tertiary-butyloxycarbonyl and octyloxycarbonyl. The term "(1–10C)alkanoyl" as used herein means straight and branch chain 1-oxoalkyls containing from one to ten carbon atoms and includes, for example, acetyl, 4-methylpentanoyl and octanoyl. The term "phenyl(1–10) alkanoyl as used herein means phenyl substituted 1-oxoalkyl radicals wherein the 1-oxoalkyl portion thereof is a straight or branched chain 1-oxoalkyl containing from one to ten carbon atoms; for example, 1-oxo-3-phenylpropyl and 1-oxo-5-methyl-6-phenylhexyl.

The symbol "Ψ[CSNH]" used between the three-letter representations of two amino acid residues means that the normal amide bond between those residues in the peptide, being represented, has been replaced with a thioamide bond.

Additional abbreviations or symbols used hereafter are:

| | |
|---|---|
| Boc | 1,1-methylethoxycarbonyl or tertiary-butyloxycarbonyl |
| DAT | desaminotyrosyl or 1-oxo-3-(4-hydroxyphenyl)phenylpropyl |
| Ph | phenyl |
| PhCH$_2$CH—CO | 1-oxo-3-phenylpropyl |
| N—Me—Val | N-methylvalyl residue |
| Tbg | tertiary-butylglycine or 2(S)-amino-3,3-dimethylbutanoic acid residue |
| Asp(cyBu) | (S)-α-amino-1-carboxycyclobutaneacetic acid residue |
| Asp(cyPn) | (S)-α-amino-1-carboxycyclopentaneacetic acid residue |

The term "pharmaceutically acceptable carrier" or "veterinarily acceptable carrier" as use herein means a non-toxic, generally inert vehicle for the active ingredient which does not adversely affect the ingredient.

The term "physiologically acceptable carrier" as used herein means an acceptable cosmetic vehicle of one or more non-toxic excipients which do not react with or reduce the effectiveness of the active ingredient contained therein.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "effective amount" means a predetermined antiviral amount of the antiviral agent, i.e. an amount of the agent sufficient to be effective against the viral organisms in vivo.

The term "coupling agent" as used herein means an agent capable of effecting the dehydrative coupling of an amino acid or peptide free carboxy group with a free amino group of another amino acid or peptide to form an amide bond between the reactants. Similarly, such agents can effect the coupling of an acid and an alcohol to form corresponding esters. The agents promote or facilitate the dehydrative coupling by activating the carboxy group. Descriptions of such coupling agents and activated groups are included in general text books of, peptide chemistry; for instance, E. Schroder and K. L. Lubke, "The Peptides", Vol. 1, Academic Press, New York, N.Y., 1965, pp 2–128, and K. D. Kopple, "Peptides and Amino acids", W. A. Benjamin, Inc., New York, N.Y., 1966, pp 33–51. Examples of coupling agents are thionyl chloride, diphenylphosphoryl azide, 1,1'-carbonyldiimidazole, dicyclohexylcarbodiimide, N-hydroxysuccinimide, or 1-hydroxybenzotriazole in the presence of dicyclohexylcarbodiimide. A very practical and useful coupling agent is (benzotriazol-1-yloxy)tris(dimethylamino)-phosphonium hexafluorophosphate, described by B. Castro et al., Tetrahedron Letters, 1219 (1975), see also D. Hudson, J. Org. Chem., 53, 617 (1988), either by itself or in the presence of 1-hydroxybenzotriazole.

Process

The peptides of formula 1 can be prepared by processes which incorporate therein methods commonly used in peptide synthesis such as classical solution coupling of amino acid residues and/or peptide fragments, and if desired solid phase techniques. Such methods are described, for example, by E. Schroder and K. Lubke, cited above, in the textbook series, "The Peptides: Analysis, Synthesis, Biology", E. Gross et at., Eds., Academic Press, New York, N.Y., 1979–1987, Volumes 1 to 8, and by J. M. Stewart and J. D. Young in "Solid Phase Peptide Synthesis", 2nd ed., Pierce Chem. Co., Rockford, Ill., USA, 1984.

A common feature of the aforementioned processes for the peptides is the protection of the reactive side chain groups of the various amino acid residues or derived amino acid residues with suitable protective groups which will prevent a chemical reaction from occurring at that site until the protective group is ultimately removed. Usually also common is the protection of an α-amino group on an amino acid or a fragment while that entity reacts at the carboxy group, followed by the, selective removal of the α-amino protective group to allow subsequent reaction to take place at that location. Usually another common feature is the initial protection of the C-terminal carboxyl of the amino acid residue or peptide fragment, if present, which is to become the C-terminal function of the peptide, with a suitable protective group which will prevent a chemical reaction from occurring at that site until the protective group is removed after the desired sequence of the peptide has been assembled.

In general, therefore, a peptide of formula 1 can be prepared by the stepwise coupling in the order of the sequence of the peptide of the amino acid or derived amino acid residues, or fragments of the peptide, which if required are suitably protected, and eliminating all protecting groups, if present, at the completion of the stepwise coupling to obtain the peptide of formula 1. More specific processes are illustrated in the examples hereinafter.

The peptide of formula 1 of this invention can be obtained in the form of a therapeutically acceptable salt.

In the instance where a particular peptide has a residue which functions as a base, examples of such salts are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phorphoric acid. If desired, a particular acid addition salt is convened into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In the instance where a particular peptide has one or more free carboxy groups, examples of such salts are those with the sodium, potassium or calcium cations, or with strong organic bases, for example, triethylamine or N-methylmorpholine.

Antiherpes Activity

The antiviral activity of the peptides of formula 1 can be demonstrated by biochemical, microbiological and biological procedures showing the inhibitory effect of the compounds on the replication of herpes simplex viruses, types 1 and 2 (HSV-1 and HSV-2), and other herpes viruses, for example, varicella zoster virus (VZV), Epstein-Barr virus (EBV), equine herpes virus (EHV) and cytomegalovirus.

Noteworthy is the fact that all of the aforementioned viruses are dependent on their own ribonucleotide reductase to synthesize deoxyribonucleotides for their replication. Although this fact may not be directly linked with the antiviral activity found for the present peptides, the latter compounds have been shown so far to have antiviral properties against all viruses dependent on ribonucleotide reductase to synthesis DNA for their replication.

In the examples hereinafter, the inhibitory effect on herpes ribonucleotide reductase is noted for exemplary peptides of formula 1. Noteworthy, in the connection with this specific inhibition of herpes ribonucleotide reductase, is the relatively minimal effect or absence of such an effect of the peptides on cellular ribonucleotide reductase activity required for normal cell replication.

A method for demonstrating the inhibitory effect of the peptides of formula 1 on viral replication is the cell culture technique; see, for example, T. Spector et al., Proc. Natl. Acad. Sci. USA, 82, 4254 (1985).

The therapeutic effect of the peptides can be demonstrated in laboratory animals, for example, by using an assay based on genital herpes infection in Swiss Webster mice, described by E. R. Kern, et al., Antiviral Research, 3, 253 (1983).

When a peptide of this invention, or one of its therapeutically acceptable salts, is employed as an antiviral agent, it is administered topically or systemically to warm-blood animals, e.g. humans, pigs or horses, in a vehicle comprising one or more pharmaceutically acceptable carriers, the proportion of which is determined by the solubility and chemical nature of the peptide, chosen route of administration and standard biological practice. For topical administration, the peptide can be formulated in pharmaceutically accepted vehicles containing 0.1 to 10 percent, preferably 0.5 to 5 percent, of the active agent. Such formulations can be in the form of a solution, cream or lotion.

For systemic administration, the peptide of formula 1 is administered by either intravenous, subcutaneous or intramuscular injection, in compositions with pharmaceutically acceptable vehicles or carriers. For administration by injection, it is preferred to use the peptide in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's Pharmaceutical Sciences", 16th ed, Mack Publishing Company, Easton, Pa., 1980.

The dosage of the peptide will vary with the form of administration and the particular active agent chosen. Furthermore, it will vary with the particular host under treatment. Generally, treatment is initiated with small increments until the optimum effect under the circumstances is reached. In general, the peptide is most desirably administered at a concentration level that will generally afford antivirally effective results without causing any harmful or deleterious side effects.

With reference to topical application, the peptide is administered cutaneously in a suitable topical formulation to the infected area of the body e.g. the skin or part of the oral or genital cavity, in an mount sufficient to cover the infected area. The treatment should be repeated, for example, every four to six hours until lesions heal. Healing results usually within 3 to 4 days. No contraindications have been observed.

With reference to systemic administration, the peptide of formula 1 is administered at a dosage of 10 mcg to 1000 mcg per kilogram of body weight per day, although the aforementioned variations will occur. However, a dosage level that is in the range of from about 100 mcg to 500 mcg per kilogram of body weight per day is most desirably employed in order to achieve effective results.

Another aspect of this invention comprises a cosmetic composition comprising a herpes viral prophylactic amount of the peptide of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nightly to susceptible areas of the skin. Generally, the cosmetic composition contains less of the peptide than corresponding pharmaceutical compositions for topical application. A preferred range of the amount of the peptide in the cosmetic composition is 0.01 to 0.2 percent by weight.

Although the formulation disclosed hereinabove am effective and relatively safe medications for treating herpes viral infections, the possible concurrent administration of these formulations with other antiviral medications or agents to obtain beneficial results is not excluded. Such other antiviral medications or agents include acyclovir and antiviral surface active agents or antiviral interferons such as those disclosed by S. S. Asculai and F. Rapp in U.S. Pat. No. 4,507,281, Mar. 26, 1985.

The following examples illustrate further this invention. Solution percentages or ratios express volume to volume relationship, unless stated otherwise. Abbreviations used in the examples include Boc: t-butyloxycarbonyl; BOP: (benzotriazol-1-yloxy)tris(dimethylamino)-phosphonium hexafluorophosphate; Bzl: benzyl; $CH_2Cl_2$: methylene-dichloride; DAT: desaminotyrosyl or 1-oxo-3-(4-hydroxyphenyl)propyl; DIPEA: diisopropylethylamine; DMF: dimethyl formamide; $Et_2O$: diethyl ether;, EtOAc: ethyl acetate; EtOH: ethanol; HOBt: 1-hydroxybenzotriazole; HPLC: high performance liquid chromatography: MeOH: methanol; TFA: trifluoroacetic acid. Temperatures are given in degrees centigrade.

EXAMPLE 1

Preparation of the Intermediate Boc-2(S)-Amino-4-oxo-undecanoic Acid

Boc-Asp-OBzl (500 mg, 1.55 mmol) was dissolved in acetonitrile (10 ml) and N,N'-carbonyldiimidazole (277 mg, 1.71 mmol) was added to the solution. After 30 min, p-nitrobenzylmagnesium malonate (860 mg, 1.71 mmol) was added and the mixture was stirred at room temperature (20°–220C.) for 1.5 h. The acetonitrile was evaporated. The residue was dissolved in EtOAc, washed with 1N aqueous HCl, water and then brine. The organic phase was dried ($MgSO_4$) and concentrated under reduced pressure. The resulting residue was purified by chromatography ($SiO_2$, eluent: hexane-EtOAc) to give Boc-2(S)-amino-4-oxo-1,6-hexanedioic acid 1-benzyl ester 6-(4-nitrophenyl)methyl ester (600 mg, 80%). The latter compound (3.25 g, 6.5 mmol) was dissolved in DMF (40 ml). $Cs_2CO_3$ (2.33 g, 7.14 mmol) and hexyl iodide (1.51 g, 7.14 mmol) were added to the solution. The mixture was stirred at room temperature for 18 h. The solvent was evaporated. The residue was dissolved in EtOAc. The solution was washed with 1N aqueous HCl and $H_2O$, dried ($MgSO_4$) and evaporated. The residue was purified by chromatography ($SiO_2$, eluent= hexane-EtOAc) to give Boc-2(S)-amino-4-oxo-5-[(4-nitrophenyl)methoxycarbonyl]undecanoic acid benzyl ester (630 mg). A solution of the latter compound (630 mg) in MeOH (25 ml) was shaken on a Parr apparatus under an atmosphere of $H_2$ in the present of 20% $Pd(OH)_2/C$ (70 mg) for 18 h. After filtration and concentration of the reaction mixture, the resulting residue was dissolved in EtOAc. The solution was stirred with 1N aqueous HCl for 10 min. The organic phase was separated, washed with $H_2O$, dried ($MgSO_4$) and evaporated. The residue was purified by chromatography ($SiO_2$, eluent: hexane-EtOAc) to give the title compound (150 mg). NMR and MS of the product were in agreement with the expected structure.

The coupling of title compound with appropriate units for the preparation of peptides of formula 1 was achieved with DCC/HOBt as the coupling agent.

EXAMPLE 2

Preparation of the Intermediate Boc-2(S)-Amino-5-cyclopentyl-4-oxocyclopentanoic Acid Boc-2(S)-amino-4-oxo-1,6-hexanedioic acid 1-benzyl ester 6-(4-nitrophenyl)methyl ester (4.8 g, 9.6 mmol) was dissolved in DMF (100 ml). Na$_2$CO$_3$ (4.07 g, 38.4 mmol) and 1,4-diiodobutane (3.59 g, 11.6 mmol) were added to the solution. The mixture was stirred 18 h at room temperature and then heated at 50° for 3 h. Evaporation of the reaction mixture, extraction of the resulting residue with EtOAc, washing of the extract with 1N aqueous HCl and water, drying (MgSO$_4$) and evaporation of the extract gave a crude product. The crude product was purified by chromatography (SiO$_2$, eluent: hexane-EtOAc) to give the corresponding benzyl ester of the title compound (4.3 g). The benzyl ester of the latter compound was subjected to hydrogenolysis [5% Pd(OH$_2$)/C in MeOH, 18 h] and worked up (see example 1) to give the title compound (140 mg). NMR and MS of the product were in agreement with the expected structure.

The coupling of the title compound with other appropriate units for the preparation of peptides of formula 1 was achieved with BOP, see hereinafter.

Analogous derived amino acid intermediates having a ketone in their side chain were prepared in a similar manner as described for example 1 and 2 using the appropriate alkyl iodide.

EXAMPLE 3

Preparation of the Intermediate Boc-Asp(OBzl)Ψ[CSNH]Leu-OBzl

A stirred mixture of Boc-Asp(OBzl)Leu-OBzl (2.90 g, 5.51 mmol) and Lawesson's reagent (1.12 g, 2.7 mmol), see "U. Pederson et al., Tetrahedron, 38, 3267 (1982), in toluene (30 ml) was heated at reflux for 2 h. Column chromatography with SiO$_2$ (3.5×30 cm) and elution with CH$_2$Cl$_2$ gave the title compound (2.0 g), MS: 543 (M+H)$^+$, as a yellow oil (major fraction).

Analogous thioamides were prepared in the same manner and incorporated into the appropriate peptides of formula 1 according to conventional solution phase peptide synthesis.

EXAMPLE 4

Preparation of 3-Alkyl- or 3,3-Dialkyl-L-aspartic Acid Intermediates and (S)-α-Amine-1-carboxycycloalkylacetic Acid Intermediates These intermediates, for example, Boc-Asp(cyPn)(OBzl)-OH, were prepared according the method of M. Bochenska and J. F. Biernat, Rocz. Chem., g 1195 (1976); see Chem. Abstr., 86, 43990r (1977). More specifically exemplified, (±)-Boc-Asp(cyPn)(OBzl)-OH was prepared as follows: To a solution of 1-bromocyclopentane-carboxylic acid ethyl ester [17.1 g, 77.3 mmol, described by D. N. Harpp et al., J. Org. Chem., 46, 3420 (1975)] and freshly distilled ethyl isocyanoacetate (12.7 g, 122 mmol) in a mixture of dimethylsulfoxide and Et$_2$O (1:1, 120 ml) was added sodium hydride (4.5 g, 60% dispersion in mineral oil, 122 mmol) in small portions over 5 h. The resulting red slurry was stirred at room temperature for 16 h after which time it was treated with a saturated aqueous solution of ammonium chloride (5 ml). The mixture was diluted with water (500 ml). The resulting mixture was extracted (2×) with ethyl acetate. The ethyl acetate layers were combined and washed with water (2×) and then with brine. Drying (MgSO$_4$), filtering and concentration of the extract afforded a dark red oil. This material was flash chromatographed through a 5×25 cm column of silica gel [eluent: ethyl acetate-hexane (1:10)]. Concentration of the appropriate fractions provided α-cyano-1-carboxycyclopentaneacetic acid diethyl ester as a clear colorless viscous liquid (13 g, 66%).

The latter compound (13 g, 51 mmol) was mixed with 6N aqueous HCl (60 ml) at 0°. After dissolution, the reaction mixture was heated in a oil barb at 120° for 24 h. After this time water was removed from the mixture using a dry ice rotory evaporator. The resulting white solid was dried under high vacuum for 18 h. The dried material was dissolved in a mixture of dioxane (50 ml) and 3N aqueous NaOH (52 ml). A solution of di(tertiarybutyl) dicarbonate (14.6 g, 67 mmol) in dioxane (25 ml) was added to the solution. The mixture was stirred at room temperature for 16 h. Additional 3N aqueous NaOH was added at intervals insuring a pH of about 10. The mixture was diluted with water (500 ml) and extracted (2×) with Et$_2$O (200 ml). The aqueous phase was rendered acidic (pH=3) with solid citric acid and extracted (2×) with ethyl acetate (300 ml). The combined ethyl acetate extracts were washed with water (3×) and brine. Drying, filtering and concentration of the extract afforded Boc-Asp (cyPn)-OH as a white solid (14 g, 96%).

To a solution of the latter compound (7.2 g, 25 mmol) in dry DMF (50 ml) was added K$_2$CO$_3$ (7.6 g, 55 mmol) and benzyl bromide (6.6 ml, 55 mmol). The reaction mixture was stirred at room temperature for about 7 h. Thereafter, the reaction mixture was poured into a mixture of water (500 ml) and ethyl acetate (350 ml). The organic phase was washed with water (2×) and brine. Drying, filtering and concentration of the extract provided a pale yellow viscous liquid. This material was flash chromatographed through a 5×20 cm column of silica gel, eluting with hexane-ethyl acetate (12:1). Concentration of the appropriate fractions provided the dibenzyl derivative of Boc-Asp-(cyPn)-OH as a low melting white solid (11 g, 94%). The dibenzyl product was dissolved in TKF (100 ml) and an aqueous solution of LiOH (23.5 ml, 1N) was added. After 4 h, the reaction mixture was poured into water and extracted (3×) with Et$_2$O. The aqueous phase was rendered acidic with 10% aqueous citric acid and extracted (2×) with ethyl acetate. The ethyl acetate layers were combined, dried (MgSO$_4$), filtered and concentrated to provide Boc-Asp(cyPn)(OBzl)-OH as a clear color less gum (7.3 g, 82%).

EXAMPLE 5

General Procedure for the Solid Phase Preparation of Peptides of Formula 1

A modified version of the solid phase method of R. B. Merrifield, J. Am. Chem. Soc., 85, 2149 (1963) was used to prepare the peptides, preferably using a BHA-photoresin such as [4-(2-chloropropionyl)phenoxy]acetamidomethyl-copoly(styrene-1% divinylbenzene) resin, see D. Bellof and M. Mutter, Chemia, 39, 317 (1985). Protection of free carboxy groups and hydroxy groups was provided by the Bzl protective group. Typically, a Boc-amino acid, representing the C-terminal unit of the desired peptide, e.g. Boc-Leu-OH, was linked to the above noted BHA-photoresin by the potassium fluoride method of K. Horiki et al., Chem. Lea., 165 (1978), using 9 molar equivalents of KF and 3.6 molar equivalents of Boc-Leu-OH., for example, in DMF at 70° C. for 24 h to give [4-{2-(Boc-leucine)propionyl}phenoxy]acetamidomethyl-copoly(styrene-1% divinylbenzene) resin. The dried amino acid-solid support typically showed a leucine content of 0.6 to 0.8 mmol/g for the product, as determined by deprotection of an aliquot, followed by picric acid titration, B. F. Gisin, Anal. Chim. Acta, 58, 248 (1972). The latter amino acid-solid support was used to build up the required sequence of units (i.e. amino acid residues, derived amino acid residues) of the desired peptide by solid phase methodology. Two molar equivalents (per mole of the amino acid-solid support) of the appropriate amino acid residues were coupled serially with the solid support system using BOP (2 molar equivalents), or BOP (2 molar equivalents)/HOBt (1 molar equivalent), in the presence of N-methylmorpholine (6 molar equivalents) in dry DMF. Completion of coupling was verified by a negative ninhydrin test, E. Kaiser et al., Anal Biochem., 34, 595 (1979). Double coupling was used when necessary.

Cleavage of the protected peptide from the solid support was accomplished by irradiation at 330 nm in EtOH/DMF (1:4) at 0° under an argon atmosphere for 6 to 18 h. Protective groups (Bzl), if present, were removed from the cleavage product by hydrogenolysis over 5% or 10% Pd/C or 20% Pd(OH)$_2$/C by standard procedures (cf. example 1). Purification of the final product was performed by reversed-phase HPLC to better than 95% homogeneity using 0.06% aqueous TFA/acetonitrile gradients.

More specifically exemplified, the protected peptide, PhCH:CH$_2$CO-N-Me-Val-Ile—NHCH(2-oxononyl)-CO-Asp(OBzl)-Leu-OH was assembled by the preceding procedure on a BHA photoresin using BOP/HOBt as the coupling agent and the intermediate of example 1, followed by cleavage of the resulting protected peptide resin by photolysis under argon at −5° for 6 h. DMF:EtOH(4:1) was used as the photolysis medium. Deprotection of the cleavage product was effected by hydrogenolysis using 5% Pd/C as catalyst. Purification of the product was done by HPLC, the product being dissolved in 0.1N aqueous NH$_4$H solution and the solution adjusted to pH$_6$ with 0.1N aqueous AcOH. Whatman Partisil® 100DS-3 C-18 column (2.2×50 cm$^2$), 10 micron particle size, was used. Elution was done with a gradient of acetonitrile and 0.06% aqueous TFA. Pure fractions (determined by analytical HPLC) were pooled and lyophilized to give PhCH$_2$CH$_2$CO-N-Me-Val-Ile-NHCH(2-oxononyl)-CO-Asp-Leu-OH. MS: 824 (M+Na)$^+$.

In the same manner but replacing the intermediate of example 1 with the intermediate of example 2, PhCH$_2$CH$_2$CO-N-Me-Val-Ile-NHCH(2-cyclopentyl-2-oxoethyl)-CO-Asp-Leu-OH was obtained. MS: 773 (M+H)$^+$.

The above procedure was used to prepare other peptides of formula 1. Commercially available Boc-amino acids were used. Unnatural amino acids were used in their Boc protected form; they were either commercially available, readily prepared from commercially available corresponding amino acids by reaction with di-tertiary-butyl carbonate, or prepared by standard methods.

EXAMPLE 6

Inhibition of Herpes Simplex Virus (HSV, type 1) Ribonucleotide Reductase a) Preparation of Enzyme HSV-1 ribonucleotide reductase (partially purified) was obtained from quiescent BHK-21/C13 cells infected with strain F HSV-1 virus at 10 plaque forming units/cell as described by E. A. Cohen et al., J. Gen. Virol., 66, 733 (1985).

b) Assay and Results for Exemplified Peptides

The procedure described by P. Gaudreau et al., J. Biol, Chem., 262, 12413 (1987), was employed. Results obtained for exemplified peptides of formula 1 are listed below. The assay result for each peptide is expressed as the concentration of the peptide producing 50% of the maximal inhibition (IC$_{50}$) of enzyme activity. The number of units of the enzyme preparation used in each assay was constant, based on the specific activity of the enzyme preparation. The results are relative to the activity obtained in control experiments without peptide and represent the mean of four assays that varied less than 10% with each other.

| PEPTIDE | IC$_{50}$(μM) |
|---|---|
| PhCH$_2$CH$_2$CO—N—Me—Val—Ile—NHCH(2-oxononyl)-CO—Asp—Leu—OH | 0.42 |
| PhCH$_2$CH$_2$CO—N—Me—Val—Ile—NHCH(2-cyclopentyl-2-oxoethyl)-CO—Asp—Leu—OH | 0.18 |
| PhCH$_2$CH$_2$CO—N—Me—Val—Ile—NHCH(2-oxotridecyl)-CO—Asp—Leu—NH$_2$ | 6.3 |
| 2-Ethylbutanoyl-Ile—NHCH(2-oxotridecyl)-CO—Asp—Leu—OH | 8.5 |
| PhCH$_2$CH$_2$CO—N—Me—Val—Ile—NHCH(2-oxopropyl)-CO—Asp—Leu—OH | 1.3 |
| 2-Ethylbutanoyl-Ile—NHCH(2-oxononyl)-CO—Asp—Leu—OH | 24 |
| 2-Ethylbutanoyl-Tbg—NHCH(2-oxoheptyl)-CO—Asp—Leu—OH | 7.5 |
| 2-Ethylbutanoyl-Tbg—NHCH(2-oxononyl)-CO—Asp—Leu—OH | 4.5 |
| 2-Ethylbutanoyl-Tbg—NHCH(2-oxononyl)-CO—NHCH[C(CH$_3$)$_2$COOH]—CO—Leu—OH | 1.2 |
| 2-Ethylbutanoyl-Tbg—NHCH(2-cyclopentyl-2-oxoethyl)-CO—Asp—NHCH$_2$CH$_2$C(CH$_3$)$_3$ | 23 |

Other examples of the peptides of this invention are:

2-Biphenylcarbonyl-Val-Ile-(N-Me)-CH[4(R)-methyl-2-oxooctyl]-CO-Asp-Leu-OH

Octanoyl-N-Me-Val-NHCH(3-cyclohexyl-2-oxopropyl)-CO-NHCH-[CH(CH$_3$)COOH]-CO-NHCH[CH$_2$CH(CH$_3$)$_2$]-5-1H-tetrazole[1]

(3,4-Dihydroxy-Ph)CH$_2$CO-N-Me-Val-Ile-NHCH(2-oxo-5-phenylpentyl)-CO-Asp-leucinol PhCH$_2$CH$_2$CO-N-Me-Val-Ile-NHCH(2-oxodecyl)-CO-AspΨ[CSNH]-Leu-OH PhCH$_2$CH$_2$CO-Ile-N-Me-CH(2-oxononyl)-CO-Asp-Leu-OH Boc-N-Et-Val-Thr-NHCH(6-methyl-2-oxoheptyl)-CO-Asp-Leu-NHOH[2]

DAT-Ile-NHCH(2-oxo-5-phenylpentyl)-CO-Asp-Leu-N(CH$_3$)OH[2]

PhCH$_2$CH, CO-N-Me-Val-Ile-NHCH(2-oxoundecyl)-CO-Asp-Leu-OH

PhCH$_2$CH$_2$CO-N-Me-Val-Ile-NHCH(2-oxotridecyl)-CO-Asp-Leu-OH

4-Methylpentanoyl-N-Me-Val-Ile-NHCH(2-oxotridecyl)-CO-Asp-Leu-OH

4-Methylpentanoyl-Ile-NHCH(2-oxopropyl)-CO-Asp-Leu-OH

4-Methylpentanoyl-Ile-N(CH$_3$)CH(2-oxononyl)-CO-Asp-Leu-OH

PhCH$_2$CH$_2$CO-Tbg-NHCH(2-oxononyl)-CO-NHCH[C(C$_2$H$_5$)$_2$COOH]-NHCH$_2$CH$_2$CH(CH$_3$)$_2$ 2-Ethylbutanoyl-Tbg-NHCH(2-cyclohexyl-2-oxoethyl)-CO-Asp(cyBu)-Leu-OH 2-Ethylbutanoyl-Ile-NHCH(2-oxononyl)-CO-Asp(cyPn)-Leu-OH (1) The tetrazole residue or unit for this peptide was derived from Boc-Leu-NH$_2$ in the following manner: Boc-Leu-NH$_2$ was converted to the corresponding nitrile derivative by treatment with p-toluenesulfonyl chloride in CH$_2$Cl$_2$ in the presence of excess pyridine and a catalytic amount of 4-dimethylaminopyridine (Fieser and Fieser, "Reagents for Organic Synthesis", John Wiley and Sons, Inc., New York, N.Y., USA, 1967, vol 1, p 1183). The nitrile derivative then was mixed with tributyl tin azide, J. G. A. Luijten et al., Rec. Trav., 81, 202 (1962), giving a tetrazole tin derivative (cf. K. Sisido et al., Journal of Organometallic Chemistry, 33, 337 (1971). The latter was treated with HCl gas in Et$_2$O to afford the desired tetrazole residue as a hydrochloride salt which was used as such for the coupling with an activated amino acid.

(2) Terminal hydroxamic acids and terminal N-(lower alkyl)hyroxamic acids are obtained by coupling the corresponding protected C-terminal acid with hydroxylamine hydrochloride or N-(lower alkyl)hydroxylamine hydrochloride, respectively, using BOP/DIPEA in CH$_2$Cl$_2$, followed by the removal of any protecting groups.

The embodiments of this invention in which an exclusive property or privilege is claimed are defined as follows:

1. A peptide of formula I

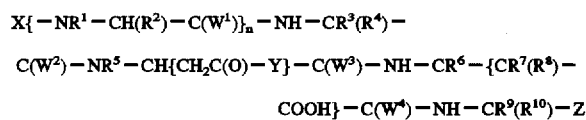

wherein
- X is 2-ethylbutanoyl or phenylpropionyl
- $R^1$ is methyl
- $R^2$ is 1-methylethyl
- $R^3$ is hydrogen
- $R^4$ is 1-methylpropyl or 1,1-dimethylethyl
- $R^5$ is hydrogen
- $R^6$ is hydrogen
- $R^7$ and $R^8$, each independently, are hydrogen or methyl
- $R^9$ is hydrogen
- $R^{10}$ is 2-methylpropyl or 2,2-dimethylpropyl
- $W^1$, $W^2$, $W^3$ and $W^4$ are oxo
- Y is methyl, pentyl, heptyl, undecyl or cyclopentyl
- Z is hydrogen, COOH or $COHN_2$ and n is the integer zero or one or a therapeutically acceptable salt thereof.

2. The peptide of claim 1 selected from the group of:

PhCH$_2$CH$_2$CO-N-Me-Val-Ile-NHCH(2-oxononyl)-CO-Asp-Leu-OH

PhCH$_2$CH$_2$CO-N-Me-Val-Ile-NHCH(2-cyclopentyl-2-oxoethyl)-CO-Asp-Leu-OH

PhCH$_2$CH$_2$CO-N-Me-Val-Ile-NHCH(2-oxotridecyl)-CO-Asp-Leu-NH$_2$

2-Ethylbutanoyl-Ile-NHCH(2-oxotridecyl)-CO-Asp-Leu-OH

PhCH$_2$CH$_2$CO-N-Me-Val-Ile-NHCH(2-oxopropyl)-CO-Asp-Leu-OH

2-Ethylbutanoyl-Ile-NHCH(2-oxononyl)-CO-Asp-Leu-OH

2-Ethylbutanoyl-Tbg-NHCH(2-oxoheptyl)-CO-Asp-Leu-OH

2-Ethylbutanoyl-Tbg-NHCH(2-oxononyl)-CO-Asp-Leu-OH

2-Ethylbutanoyl-Tbg-NHCH(2-oxononyl)-CO-NHCH{C(CH$_3$)$_2$COOH}-CO-Leu-OH or

2-Ethylbutanoyl-Tbg-NHCH(2-cyclopentyl-2-oxoethyl)-CO-Asp-NHCH$_2$CH$_2$C(CH$_3$)$_3$.

3. A pharmaceutical composition comprising a peptide as recited in claim 1, or a therapeutically acceptable salt thereof, and a pharmceutically or veterinarily acceptable carrier.

4. A cosmetic composition comprising a peptide as recited in claim 1, or a therapeutically acceptable salt thereof, and a physiologically acceptable carrier suitable for topical application.

5. A method of treating a herpes viral infection in a mammal comprising administering thereto an effective amount of a peptide as recited in claim 1, or a therapeutically acceptable salt thereof.

6. A method of claim 5 wherein the herpes viral infection is a herpes simplex viral infection.

* * * * *